United States Patent [19]
Grabenkort et al.

[11] Patent Number: 5,382,229
[45] Date of Patent: Jan. 17, 1995

[54] IRRIGATION SOLUTION RE-CIRCULATING SYSTEM

[75] Inventors: Richard W. Grabenkort, Barrington; Robert J. Kruger, McHenry; Joaquin Mayoral, Downers Grove; Sheldon M. Wecker, Libertyville, all of Ill.

[73] Assignee: Abbott Laboratories, Abbott Park, Ill.

[21] Appl. No.: 124,734

[22] Filed: Sep. 21, 1993

[51] Int. Cl.$^6$ ............................................. A61M 1/00
[52] U.S. Cl. ............................................ 604/27; 604/30
[58] Field of Search ................. 604/22, 30, 27, 28, 604/43, 405, 406, 4

[56] References Cited
FOREIGN PATENT DOCUMENTS
8706471 11/1987 WIPO ........................... 604/405

*Primary Examiner*—Jerome L. Kruter
*Attorney, Agent, or Firm*—A. Nicholas Trausch

[57] ABSTRACT

An irrigation solution re-circulating system comprises a reservoir of irrigation solution, a solution supply line for joining the reservoir in fluid communication with a surgery site for delivering a controlled volume, pressure, and temperature of the irrigation solution to the surgery site, and a return line for further joining the surgery site in fluid communication with the reservoir. A pump, which is preferably non-hemolyzing, is connected to the return line for returning a controlled volume of the irrigation solution from the surgery site to the reservoir. The system further comprises at least one filter connected to the return line for removing contaminants from the irrigation solution prior to return to the reservoir to permit re-circulation of the solution without impairing endoscopic visualization of the surgery site, while providing solution for expanding the surgery site to permit performance of the attendant surgical procedure.

12 Claims, 1 Drawing Sheet

IRRIGATION SOLUTION RE-CIRCULATING SYSTEM

TECHNICAL FIELD

The present invention generally relates to a solution irrigation system for use during arthroscopic surgical procedures, and more particularly to an irrigation solution re-circulating system which incorporates a series of filters for removing contaminants from the irrigation solution to permit reuse and recirculation of the irrigation solution.

BACKGROUND OF THE INVENTION

Some surgical procedures, such as knee, elbow, and shoulder arthroscopic surgeries, involve the inflation of a surgery site with irrigation solution, typically a saline-like solution, to facilitate performance of the particular surgical procedure while permitting visualization through an endoscope which is inserted into the surgery site.

Current irrigation solution management systems generally include an input connection from a reservoir or supply of the irrigation solution (typically multiple flexible containers or "bags" of solution) to a surgery site, and an output connection from the surgery site to a collector of irrigation solution drainage.

Such conventional fluid flow systems have several disadvantages. Since they are, in essence, single-pass systems, a very substantial volume of irrigation solution is ordinarily required. In addition to flushing the surgery site, the solution inevitably leaks from the site. As such, use of as much as 45 liters of irrigation solution during a two and one-half hour surgical procedure is not uncommon. Naturally, use of such significant volumes of irrigation solution requires frequent and regular replenishment of the solution supply. In the event of unforeseen delays during the surgery, there is a risk that the supply of the irrigation solution will be depleted. Furthermore, the used irrigation solution is considered to be medical waste which complicates disposal of the solution.

Accordingly, it is desirable to provide an irrigation solution re-circulation system to promote effective use of solution, facilitating both solution supply and disposal.

SUMMARY OF THE INVENTION

The present invention provides an irrigation solution recirculating system which comprises a reservoir of irrigation solution, a solution supply line for joining the reservoir in fluid communication with a surgery site for delivering a controlled volume of the irrigation solution to the surgery site, and a return line for further joining the surgery site in fluid communication with the reservoir. A pump, for example, a non-hemolyzing pump, is connected to the return line for returning the irrigation solution from the surgery site to the reservoir. The system further comprises at least one filter connected to the return line for removing contaminants from the irrigation solution prior to return to the reservoir to permit re-circulation of the solution without impairing endoscopic visualization of the surgery site. A series of filters are preferably employed, which filters may include a dialyzer filter.

The present invention further provides a method for recirculating an irrigation solution from a surgery site. The method comprises the steps of drawing irrigation solution from the surgery site, filtering the irrigation solution for removing contaminants therefrom that would otherwise obscure a viewing field of the surgery site, and directing the filtered irrigation solution back to the surgery site at a controlled pressure and flow rate. The controlled flow rate preferably ranges from 0.0 liters per minute to 1.0 liter per minute, with an average flow rate on the order of 0.25 liters per minute. In accordance with the illustrated embodiment of the present invention, the directing step includes passing the filtered irrigation solution through a reservoir of the irrigation solution.

Other features and advantages of the present invention will become readily apparent from the following detailed description, the accompanying drawings, and the appended claims.

DETAILED DESCRIPTION

Figure 1:
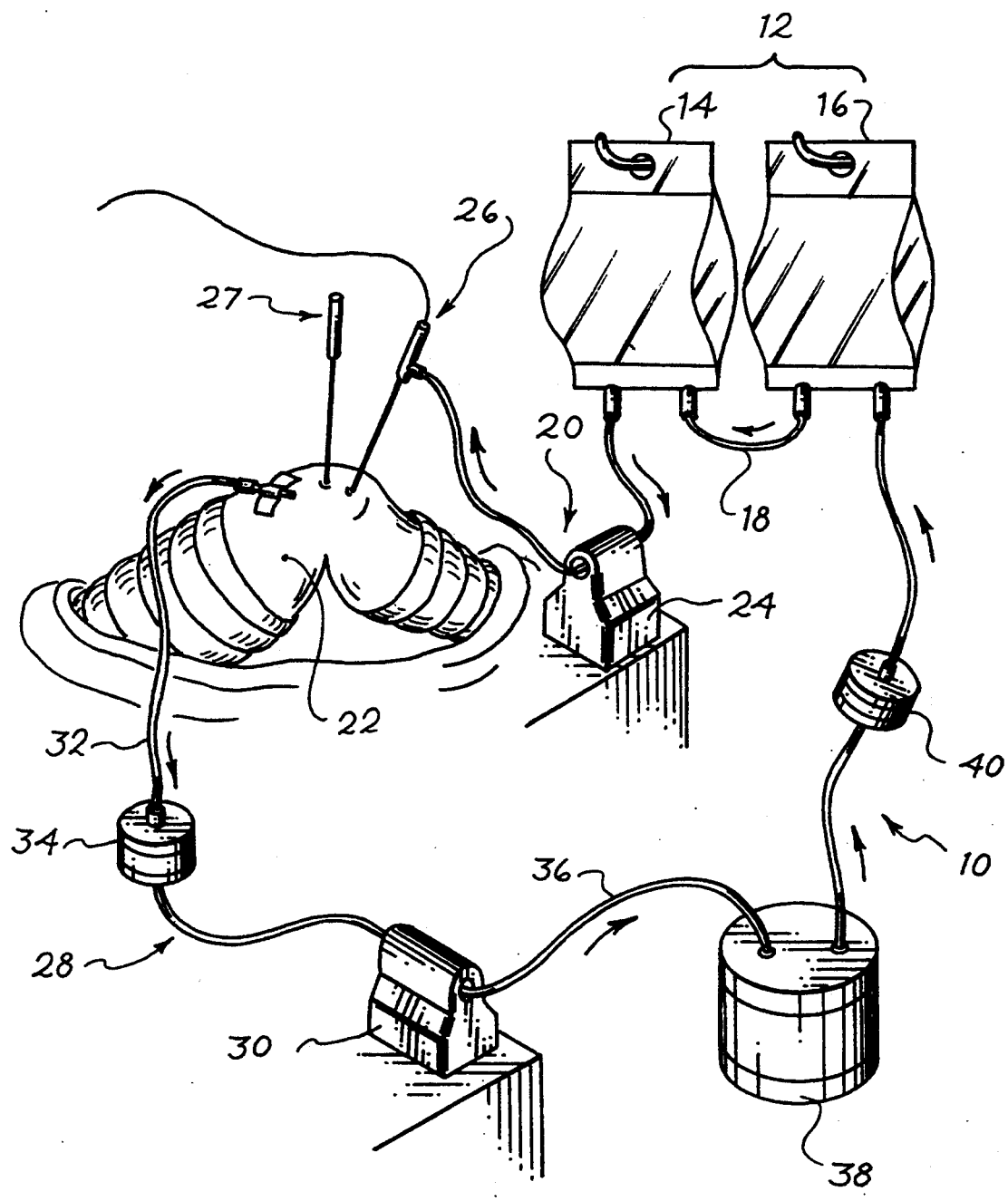
FIG. 1 is a diagrammatic view of one embodiment of an irrigation solution re-circulating system in accordance with the present invention when applied to an arthroscopic surgery.

While the present invention is susceptible of embodiment in various forms, there is shown in the drawings and will hereinafter be described an embodiment of the present invention, with the understanding that the present disclosure is to be considered as an exemplification of the invention, and is not intended to limit the invention to the specific embodiment illustrated.

Referring now to the drawing, therein is diagrammatically illustrated in FIG. 1, an irrigation solution re-circulating system 10 embodying the principles of the present invention. The system 10 as illustrated includes a reservoir 12 for containing irrigation solution, such as lactate, saline or dextrose solution. The reservoir 12 may comprise one or more flexible fluid containers 14, and has a suitable capacity of from about 6 to about 8 liters. In the illustrated embodiment, the reservoir 12 comprises two fluid containers 14, 16 which are in fluid flow communication with each other through a fluid conduit 18. The fluid containers 14, 16 can be formed of flexible plastic material, or any other suitable material known in the art.

A solution supply line 20 from one of the fluid containers 14 is coupled to a surgery site, such as to an arthroscopic surgery site 22. A pump 24 is connected to the solution supply line 20 draws irrigation solution from the reservoir 12, and direct it to the surgery site 22 (illustrated as a knee joint of a patient). An arthroscope 26 as shown in FIG. 1 is used to examine the interior of the joint and carry out diagnostic, and therapeutic procedures within the joint, which procedures can be performed with one or more suitable surgical instruments such as 27. The solution supply line 20 may also comprise a fluid supply probe or conduit, and may be connected to the arthroscope 26, such as illustrated.

A return line, generally designated 28, extends from the surgery site 22 via a pump 30 to the fluid container 16 for fluid flow communication therebetween. The return line 28 comprises a discharge conduit 32 connected between the surgery site 22 and the pump 30. The pumps 24, 30 draw a controlled stream of irrigation solution, and are preferably non-hemolyzing pumps, such as peristaltic pumps, which act to prevent destruction of red blood cells to limit discoloration of the irrigation solution. A bone chip filter 34 is preferably placed upstream of the suction pump 30 in the discharge conduit 32. The bone chip filter 34 separates bone fragments and large particulates from irrigation solution drainage. Output of the suction pump 30 is connected to the fluid container 16 through a fluid return conduit 36.

The fluid conduit 18, supply conduit 20, discharge conduit 32 and the fluid return conduit 36 can be formed of flexible, preferably transparent medical grade plastic material.

A filter 38 is connected to the fluid return conduit 36. The filter 38 separates and removes from the irrigation solution drainage molecular moieties that can otherwise obscure the viewing field of the arthroscope and impair visualization of the surgery site. The filter 38 preferably incorporates a semi-permeable membrane, and may comprise a commercially available dialyzer filter. Such a dialyzer filter 38 collects molecular moieties having a molecular weight generally ranging from about 10,000 to about 100,000, including pyrogen, white and red cells, albumin, large proteins, bacteria and the like.

Downstream of the filter 38, an additional filter, preferably an anti-bacterial, 0.2 $\mu$ filter 40 is disposed in the fluid return conduit 36. The 0.2 $\mu$ filter 40 collects bacteria, although it does not filter virus or pyrogens. Alternate filter devices can be employed, such as 0.45 $\mu$, 0.8 $\mu$ and 1.2 $\mu$ filters. The irrigation solution which has passed through those filters 38, 40 is then recirculated to the fluid container 16 as a fresh supply of irrigation solution which is subsequently delivered to the surgery site via the fluid containers 14, 16.

In a typical operation of the present system 10, about 0.5 liters of irrigation solution are initially directed into a knee joint to inflate the interior of the joint. A flow rate of the irrigation solution in the supply line is controlled by conduit and pump sizes, pump operation, to be from as little as 0.0 liters per minute, up to about 1.0 liter per minute in a continuous circulation mode of the system 10, with an average flow rate on the order of 0.25 liters per minute.

It is further contemplated that the temperature of the irrigation solution can be selectively controlled to permit cooling or warming of the surgery site. Suitable heat-exchanger means can be employed for this purpose.

The foregoing is intended as illustrative and is not to be taken as limiting. For example, although the system embodying the present invention is described in its application to arthroscopic surgery, the present irrigation fluid re-circulating system can be also effectively used for the other surgeries, such as urethral resection surgery. Still other variations, modifications and corrections can be effected without departing from the true spirit and scope of the novel concept of the present invention. It is, of course, intended to cover by the appended claims all such modifications as fall within the scope of the claims.

What is claimed is:

1. A continuous re-circulating system for recirculating a generally clear irrigation solution used in surgical procedures, comprising:
   a reservoir of irrigation solution;
   a solution supply line for joining said reservoir of irrigation solution in fluid communication with a surgery site for delivering a controlled volume of the irrigation solution to the surgery site;
   a return line for further joining the surgery site in fluid communication with said reservoir such that said reservoir, said supply line, said surgery site and said return line form a loop;
   a pump connected to said return line for returning irrigation solution from said surgery site to said reservoir of irrigation solution; and
   at least one means for filtering the solution connected to said return line for removing contaminants from said irrigation solution prior to return to said reservoir to permit re-circulation of the filtered solution to the surgery site wherein said at least one filtering mean comprises a semi-permeable membrane that removes occluding contaminants so as not to impair visualization through the solution at the surgery site.

2. The irrigation solution re-circulating system of claim 1, further comprising means for removing bone chips disposed upstream of the filtering means.

3. The irrigation solution re-circulating system of claim 2, wherein
   said means for removing bone chips is a bone chip filter and is disposed upstream of the pump.

4. The irrigation solution re-circulating system of claim 2, including
   an anti-bacterial filter in said return line for collecting bacteria.

5. The irrigation solution re-circulating system of claim 1, further comprising a second pump connected to the supply line for directing a controlled volume of the irrigation solution from the reservoir of the irrigation solution to the surgery site.

6. The irrigation solution re-circulating system of claim 1, wherein
   said reservoir of the irrigation solution comprises a supply container connected to said supply line, and a collection container connected between the return line and the supply container.

7. A method for continuous recirculation of a generally clear irrigation solution from a surgery site comprising the steps of:
   supplying an initial quantity of generally clear irrigation solution from a solution reservoir to the surgery site;
   drawing irrigation solution from the surgery site;
   filtering the irrigation solution for removing contaminants therefrom; and
   directing the filtered irrigation solution to the solution reservoir and then into the surgery site at a controlled flow rate including passing the filtered irrigation solution through a collection container and then to the reservoir of the irrigation solution wherein filtering is performed during the directing step and removes occluding contaminants from the solution.

8. The method of claim 7, wherein
   said controlled flow rate ranges from 0.0 liters per minute to about 1.0 liter per minute, with an average flow rate on the order of 0.25 liters per minute.

9. The method of claim 7, wherein
   said filtering step is performed before said passing step.

10. The method of claim 7, wherein
    in said filtering step, filtering is effected by use of a semi-permeable membrane.

11. The method of claim 10, wherein
    in said filtering step, filtering is further effected by use of a bone chip filter.

12. The method of claim 7, including
    the step of selectively controlling the temperature of said irrigation solution.

* * * * *